US00PP25177P3

(12) United States Plant Patent
Carroll et al.

(10) Patent No.: US PP25,177 P3
(45) Date of Patent: Dec. 16, 2014

(54) *ARUNDO* PLANT NAMED 'NILE FIBER'

(50) Latin Name: *Arundo donax*
Varietal Denomination: Nile Fiber

(75) Inventors: John Todd Carroll, Snohomish, WA (US); Norman Volotin, Seattle, WA (US)

(73) Assignee: TreeFree Biomass Solutions, Inc., Seattle, WA (US)

( * ) Notice: Subject to any disclaimer, the term of this patent is extended or adjusted under 35 U.S.C. 154(b) by 0 days.

(21) Appl. No.: 13/573,312

(22) Filed: Sep. 10, 2012

(65) Prior Publication Data

US 2014/0075628 P1 Mar. 13, 2014

(51) Int. Cl.
*A01H 5/00* (2006.01)

(52) U.S. Cl.
USPC ..... Plt./384

(58) Field of Classification Search
USPC ..... Plt./384
See application file for complete search history.

(56) References Cited

U.S. PATENT DOCUMENTS

PP15,489 P2 1/2005 Speichert

*Primary Examiner* — Annette Para
(74) *Attorney, Agent, or Firm* — Seed IP Law Group PLLC

(57) ABSTRACT

*Arundo donax* 'Nile Fiber' is a new and unique cultivar characterized by its lack of serrated leaf margins, vigorous growth, dark purple bands below node sections, thick wall, ease in propagation, and usefulness in biomass production such as producing superior fiber for making pulp and paper.

3 Drawing Sheets

Latin name of genus and species of plant claimed: *Arundo donax.*

Variety donomination: 'Nile Fiber'.

BACKGROUND OF THE INVENTION

The present invention relates to a new and distinct cultivar of *Arundo donax* and will be referred to hereafter by its cultivar name, 'Nile Fiber'. 'Nile Fiber' represents a new cultivar of giant reed grown for landscape and biomass production.

The inventors discovered and selected the new cultivar, 'Nile Fiber', in a cultivated garden in Kamuela, Hi. in 2007. 'Nile Fiber' was discovered as a naturally occurring cane sport of *Arundo donax*. Initially, a small cane sport was discovered that was green with a small purple band just below the node and lacking serration along the leaf margin. Subsequent cane cuttings were performed and reselected until the new cultivar was selected with a purple band just below the node and leaf margins without serrated edges. 'Nile Fiber' is unique and unlike any other known cultivars of *Arundo donax* known to the inventors.

Asexual reproduction of the new cultivar was first accomplished by cane cuttings or ramet culture in Kailua-Kona, Hi. in 2007 by the inventor. The resulting more than 2000 propagules all showed no variations from the parental stock and exhibited the same robust characteristics as the parental stock. The characteristics of this cultivar have been determined to be stable and are reproduced true to type in successive generations.

BRIEF SUMMARY OF THE INVENTION

The following characteristics of the new cultivar have been repeatedly observed and can be used to distinguish 'Nile Fiber' as a new and distinct cultivar of *Arundo* plant:

1. The foliage of 'Nile Fiber' lack serrated leaf margins. Typically, heavily serrated leaf margins are found with other ecotypes of *Arundo Donax*, such as the neighboring *Arundo donax* plants in the garden where Nile Fiber was discovered.
2. 'Nile Fiber' has almost twice as much growth as other ecotypes of *Arundo donax*. The growth habit of 'Nile Fiber' is clump-forming with a fountain-shaped bushy appearance. The growth rate of 'Nile Fiber' can be 3.5 meters of vertical growth in 25 days. 'Nile Fiber' reaches about 8 to 15 meters in height with a spread of 3 to 5 meters in 2 to 3 years when planted from a single billet section.
3. 'Nile Fiber' has a dark purple band below each node section where typically a green band is found in standard ecotypes of *Arundo donax*, such as the neighboring *Arundo donax* plants in the garden where Nile Fiber was discovered.
4. Wall thickness of 'Nile Fiber' tends to be twice as much as standard ecotypes of *Arundo donax.*
5. 'Nile Fiber' yields superior fiber for use in pulp and paper to standard ecotypes of *Arundo donax.*
6. 'Nile Fiber' is easier to propagate with at least 95% germination rates of nodal sections and ramets for the entire culm length than standard ecotypes of *Arundo donax*. Typical germination rates for ecotypes of *Arundo donax* range from 25-35%. 'Nile Fiber' shows a marked increase in nodal section germination rates when compared with other ecotypes and cultivars.

BRIEF DESCRIPTION OF THE DRAWINGS

The accompanying colored photographs illustrate the overall appearance and distinct characteristics of the new *Arundo donax* cultivar 'Nile Fiber.'

The photograph on FIG. 1 is a side view of the overall growth of 'Nile Fiber.' The plants used for this photograph reached 3 or more meters in 28 days after grown in soil from billet sections.

Figure 1:
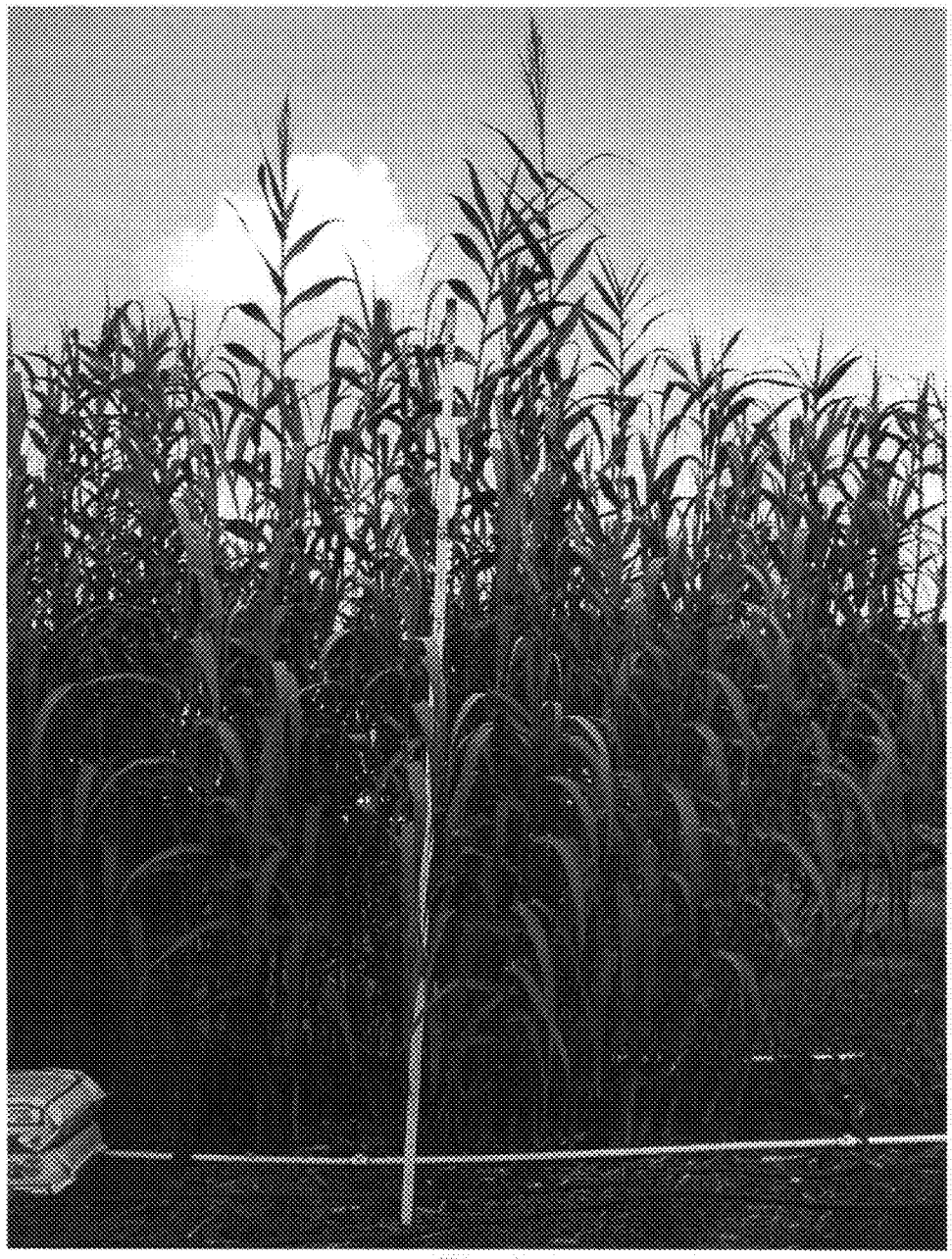
Figure 2:
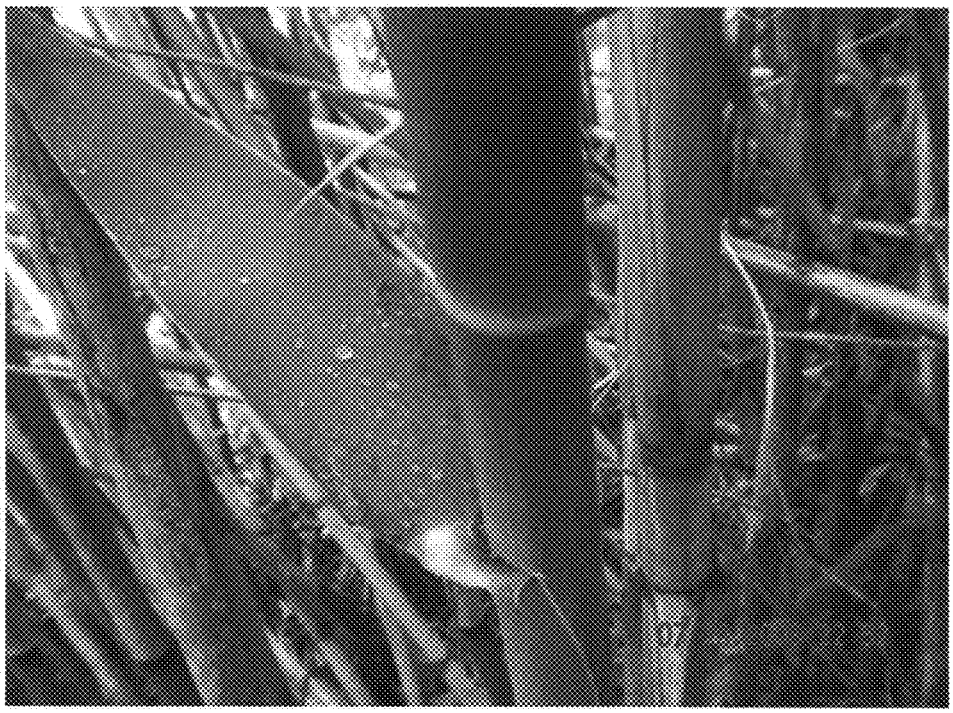

The photograph on FIG. 2 is a close-up view of a leaf showing lack of serration of leaf margins. The plant used for this photograph is a 2 year-old plant as grown in soil from a billet section.

Figure 3:
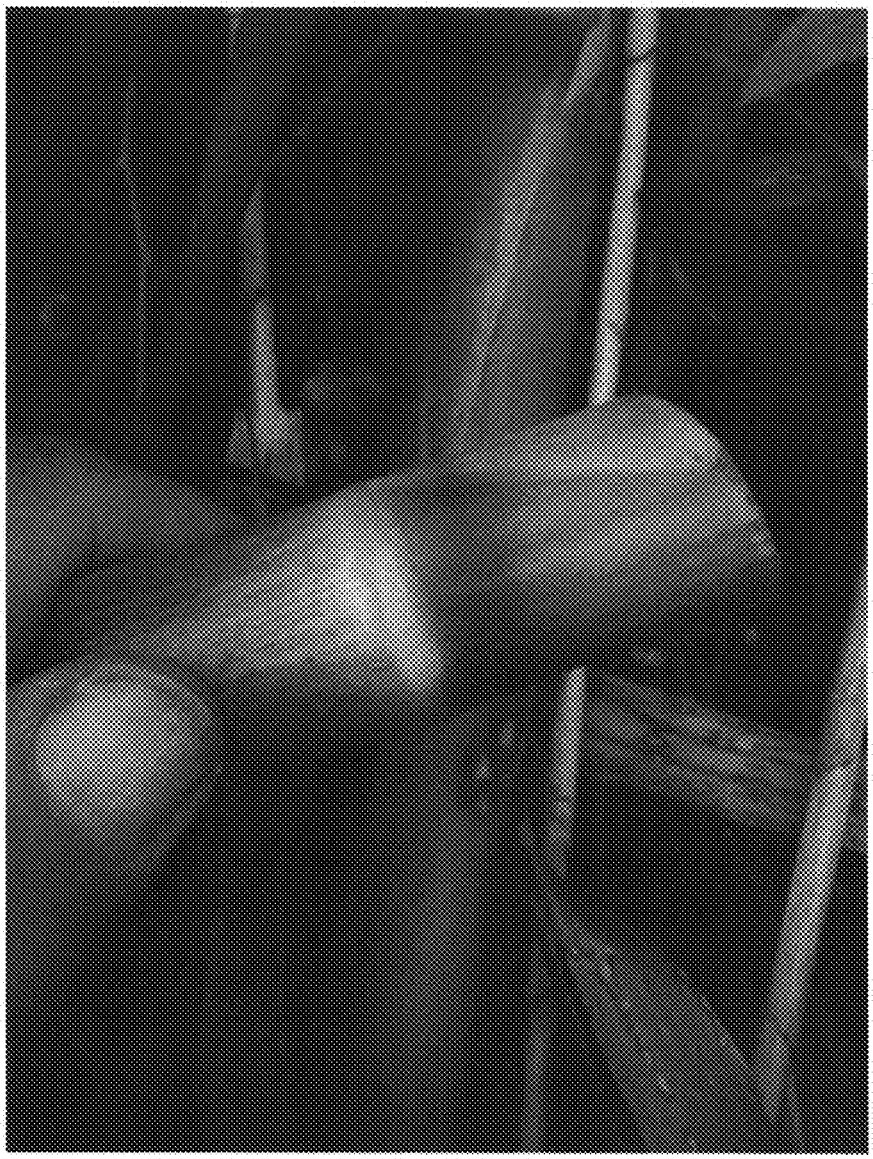

The photograph on FIG. 3 is a close-up view of a clum segment showing a dark purple band below the node section. The plant used for this photograph is a 2 year-old plant as grown in soil from a billet section.

The colors in the photographs are as close as possible with the digital photography techniques available. The color values cited in the detailed botanical description accurately describe the colors of the new *Arundo donax* cultivar 'Nile Fiber.'

DETAILED BOTANICAL DESCRIPTION

The new cultivar 'Nile Fiber' has not been observed under all possible environmental conditions to date. Accordingly, it is possible that the phenotype may vary somewhat with variation in the environment, such as temperature, light intensity, and day length, without, however, any variance in genotype.

The chart used in the identification of colors described herein is Stanford VIS Group Color Dictionary (http://vis-.stanford.edu/color-names/dictionary), except where general color terms of ordinary significance are used. Plants used in the following description were grown in an outdoor trial bed for three years from a billet section in Kailua-Kona, Hi.

Botanical classification: 'Nile Fiber' is a cultivar of *Arundo donax*.

Commercial classification: Nile Fiber giant reed grass.

Parentage: Naturally occurring cane sport of *Arundo donax*.

General description:

*Blooming habit*.—Blooms in August to November.

*Plant habit*.—Herbaceous, clump-forming, perennial ornamental grass with a fountain-like form and pendant foliage. Initial growth is un-branched until mature height is reached in late summer, branching at all cane nodes subsequently occur to create a bushy habit.

*Height and spread*.—8 to 15 meters in height with a spread of 3 to 5 meters in 2 to 3 years when planted from a billet section. Extreme, robust vigor.

*Hardiness*.—Zone 4.

*Culture*.—Growth is best when grown in moist soil in full sun.

*Diseases and pests*.—No susceptibility or resistance to diseases or pests that affect *Arundo donax* has been observed.

*Root description*.—Short, knotty rhizomes with fibrous roots.

Growth and propagation:

*Propagation*.—Tissue culture and cane cuttings, canes from immature or mature shoots. 8 mm to 1.25 cm in diameter are stripped of foliage and allowed to float in aerated water kept at 75 to 80° F. The germination rates of nodal sections and ramets are at least 95% from the entire culm length.

*Time required for root initiation*.—Rooted cane cuttings are fully developed in soil. It takes approximately 7 to 14 days to emerge and 21 to 28 days until cuttings can be taken.

*Time required for root development*.—Rooted cane cuttings will fully develop in the soil in 30 to 40 days when grown outdoors at night temperatures between 65 to 80° F. Night temperatures below 65° F. result in slower growth.

Culm (stem) description: Round, sheathed, and hollow when mature; thick, short, branched rhizomes; culms arising from large knotty creeping rootstock, terete, 2-4 cm in diameter, smooth, hollow, reed-like, many-noded, often with a white scurf; dark purple (#3a1a34) band below each node section; wall thickness 10-14 mm.

Foliage description: Leaves numerous, blades flat, smooth, 30-70 cm long, 2-7.5 cm broad on main stem, glaucous-green, drooping, tapering to a fine point, lack of serrations on leaf margins; leaf-sheaths tightly cordate-clasping, hairy tufted at base; ligules truncate, 1-2 mm long, short-ciliate; grass green on both upper and lower surfaces (#48a421).

Inflorescence description: Panicle erect, large, contracted, feathery with silky hairs, light brown or yellowish-brown, 30-70 cm long, whitish with purple hue, slightly lustrous, branches scabrous; spikelets 8-16 mm long, 2-7-flowered; florets all bisexual except the reduced uppermost one; glumes equal, narrowly lanceolate, acuminate, 3-nerved, slightly longer than florets; lemmas lanceolate, 7-10 mm long, 3-5-veined with shorter veinlets between, 2-toothed at apex, with long white hairs on back; awn between the teeth at apex, 1-3 mm long, slender, erect; callus small, broadly ovate, with short hairs 1.5-2 mm long on both sides; palea one-half to two-thirds as long as lemma; anthers 2.5-3 mm long.

The invention claimed is:

1. A new and distinct cultivar of *Arundo* plant named 'Nile Fiber' substantially as herein shown and described.

* * * * *